United States Patent [19]

Wade

[11] Patent Number: 4,478,835
[45] Date of Patent: Oct. 23, 1984

[54] SUBSTITUTED IMIDAZO[1,5-C]PYRIMIDINES

[75] Inventor: James J. Wade, Oakdale, Minn.

[73] Assignee: Riker Laboratories, Inc., St. Paul, Minn.

[21] Appl. No.: 519,707

[22] Filed: Aug. 2, 1983

[51] Int. Cl.$^3$ .................. C07D 487/04; C07D 413/04; A61K 31/505; A61K 27/00

[52] U.S. Cl. ...................................... 424/246; 544/60; 544/61; 544/117; 544/122; 544/123; 544/281; 544/309; 544/330; 544/331; 424/248.4; 424/251

[58] Field of Search .................. 544/281, 60, 61, 117, 544/122; 424/251, 246, 248.4

[56] References Cited

U.S. PATENT DOCUMENTS 3,157,655 11/1964 Takamizawa et al. ............. 424/251
4,093,617 6/1978 Robins et al. ..................... 544/281
4,153,695 5/1979 Turner .............................. 544/281

Primary Examiner—Paul M. Coughlan, Jr.
Assistant Examiner—S. A. Gibson
Attorney, Agent, or Firm—Donald M. Sell; James A. Smith; Robert W. Sprague

[57] ABSTRACT

Substituted imidazo[1,5-c]pyrimidines have been found to have potent bronchodilator activity. Pharmacological methods, pharmaceutical compositions and synthetic intermediates are also disclosed.

17 Claims, No Drawings

SUBSTITUTED IMIDAZO[1,5-c]PYRIMIDINES

TECHNICAL FIELD

The present invention relates to compounds which are named imidazo[1,5-c]pyrimidines. These compounds are substituted on any of the ring carbon atoms at positions 3, 5 and 7. This invention also relates to the pharmacological use of these compounds as bronchodilators, pharmaceutical compositions containing these compounds, and synthetic intermediates useful in preparing these compounds.

BACKGROUND OF THE INVENTION

Applicant is unaware of any imidazo[1,5-c]pyrimidines which have been reported in the literature.

DETAILED DESCRIPTION OF THE INVENTION

The present invention relates to novel imidazo[1,5-c]pyrimidines which are useful bronchodilators. The present invention also relates to pharmacological methods of using these compounds as bronchodilators, pharmaceutical compositions containing these compounds and novel synthetic intermediates useful in the preparation of these compounds.

More specifically, the present invention relates to compounds of Formula I

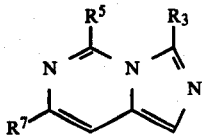

wherein $R_3$ is hydrogen, lower alkyl or phenyl; $R_5$ is chloro, amino, lower alkylamino, di(lower)alkylamino, mercapto, phenylthio, benzylthio, lower alkoxy, lower alkylthio, or

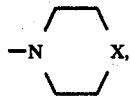

wherein X is oxygen, sulfur or methylene; and $R_7$ is hydrogen, chloro, lower alkoxy, lower alkylthio, methyl or

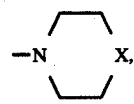

wherein X is oxygen, sulfur or methylene; and pharmaceutically acceptable acid addition salts thereof.

The phrase "lower alkyl" is defined for purposes of the instant specification and claims as designating straight and branched-chain alkyl groups containing one to about four carbon atoms. Preferred lower alkyl substituents are methyl, ethyl and propyl.

The preferred X moiety in those compounds containing the above heterocyclic substituent is oxygen or sulfur.

One presently preferred sub-class of compounds of the invention is that wherein at least one of $R_5$ and $R_7$ is lower alkoxy or lower alkylthio. These compounds are preferred because of generally higher potency in protection against histamine-induced contraction of isolated guinea pig tracheal tissue. This assay is discussed in greater detail below.

Specific preferred compounds which are active at a concentration of 10 ug per ml or lower in the above assay are:

7-methoxy-5-methylthioimidazo[1,5-c]pyrimidine 5,7-bis(methylthio)-3-methylimidazo[1,5-c]pyrimidine 7-chloro-3-methyl-5-methylthioimidazo[1,5-c]pyrimidine 7-chloro-3-isopropyl-5-(N-methylamino)imidazo[1,5-c]pyrimidine 7-chloro-3-isopropylimidazo[1,5-c]pyrimidine-5-thiol 7-chloro-3-isopropyl-5-(n-propylamino)imidazo[1,5-c]pyrimidine 5-amino-7-chloro-3-(n-propyl)imidazo[1,5-c]pyrimidine 3-(n-propyl)-5-methylthio-7-methoxyimidazo[1,5-c]pyrimidine 5-methoxy-7-methylthio-3-phenylimidazo[1,5-c]pyrimidine 3-methyl-7-methoxy-5-methylthioimidazo[1,5-c]pyrimidine 7-chloro-5-methoxy-3-(n-propyl)imidazo[1,5-c]pyrimidine 7-chloro-5-methoxy-3-methylimidazo[1,5-c]pyrimidine.

The bronchodilator activity of the compounds of Formula I was assessed by the measurement of effects on isolated tracheal spirals. This is a well known in vitro test for determining bronchodilator activity. The test was conducted as follows: Female guinea pigs were sacrificed, and each trachea was removed and cut into a spiral strip. Each strip was mounted in a constant temperature (37° C.) muscle bath of approximately 15 ml volume. The bathing medium was Krebs-Henseleit solution. Movement of the tracheal strip was measured by means of an isometric transducer connected to an electric recorder. The bath was aerated with a mixture of 95% carbon dioxide and 5% oxygen. Contractions were induced in the strips by the addition of a suitable amount of histamine, acetylcholine or barium chloride. The amount of a given compound of Formula I (measured in ug/ml) required to provide greater than 75% relaxation of the drug-induced contraction is considered an effective concentration. For comparison, a well known standard bronchodilator, aminophylline, requires concentrations of 50 ug/ml versus histamine, 100 ug/ml versus acetylcholine and 10 ug/ml versus barium chloride induced contraction.

The compounds of Formula I which were found to be most active in the in vitro test, including some of those listed above as preferred compounds, were tested in vivo in the guinea pig for oral activity using the so-called histamine aerosol method described in U.S. Pat. No. 3,248,292. This test was modified slightly in that a 0.1% aqueous solution of histamine was used as the agent for inducing bronchial constriction. Oral doses were measured in mg/kg of body weight of the guinea pig.

The compounds of Formula I may be administered to mammals in order to obtain bronchodilation. The compounds may be administered orally, parenterally or by inhalation. Preferably they are administered orally. The usual effective human dose will be 0.1 to 50 mg/kg of body weight.

Pharmaceutically acceptable acid-addition salts of compounds of Formula I are generally prepared by reaction of the respective compound with an equimolar amount of a relatively strong acid, preferably an inorganic acid such as hydrochloric, sulfuric or phosphoric acid in a polar solvent. Isolation of the salt is facilitated by the addition of a solvent in which the salt is insoluble, an example of such a solvent being diethyl ether.

The compounds of Formula I, either as free bases or in the form of a pharmaceutically acceptable acid-addition salt, can be combined with conventional pharmaceutical diluents and carriers to form such dosage forms as tablets, capsules, suspensions, solutions, suppositories and the like. The pharmaceutical carrier employed may be, for example, either a solid or liquid. Examples of suitable solid carriers are lactose, terra alba, sucrose, talc, gelatin, agar, pectin, acacia, magnesium stearate, stearic acid, and the like. Examples of suitable liquid carriers are syrup, peanut oil, olive oil, water and the like. Similarly, the carrier or diluent can include any time delay material well known to the art, such as glyceryl monostearate or glyceryl distearate, these being useful alone or, for example, in combination with a wax.

Compounds of Formula I wherein $R_3$ is as defined above; $R_5$ is lower alkoxy, lower alkylthio or

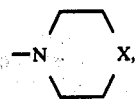

wherein X is as defined above; and $R_7$ is lower alkoxy or lower alkylthio, may be prepared as follows in Reaction Scheme I:

Reaction Scheme I

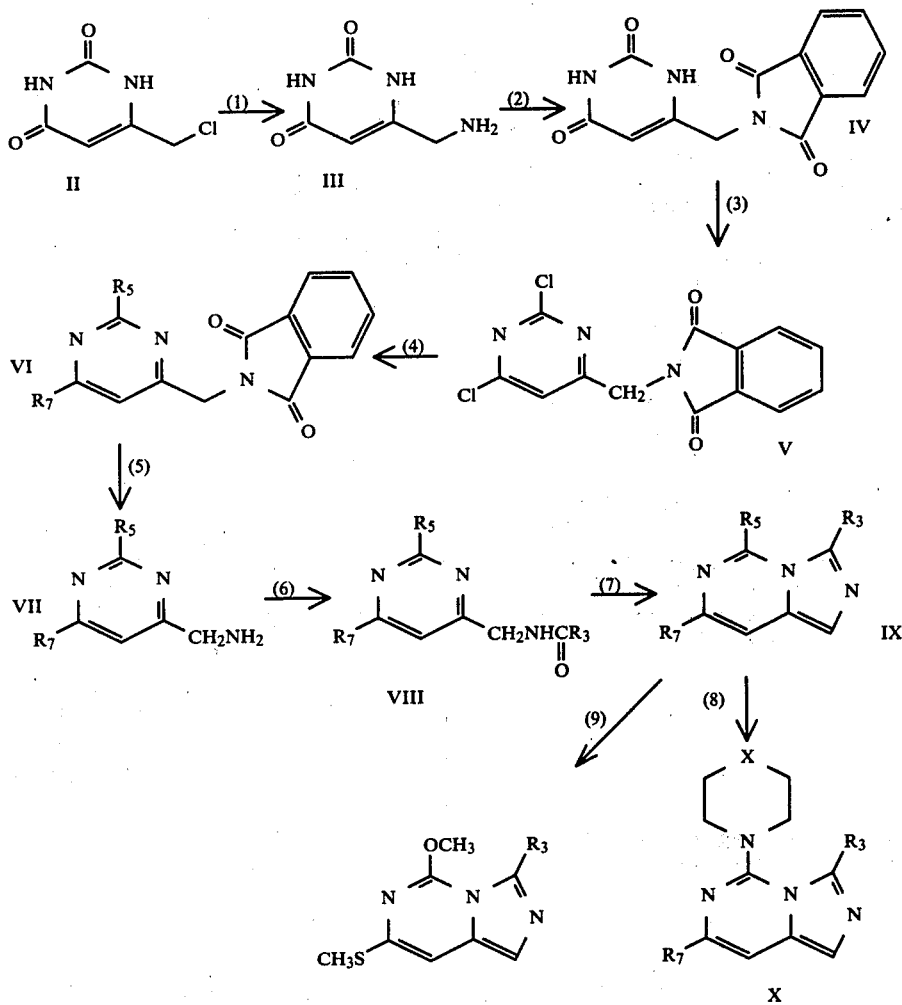

In step (1) of Reaction Scheme I, the known compound of Formula II is reacted with anhydrous ammonia to provide the compound of Formula III.

In step (2), the compound of Formula III is reacted with phthalic anhydride to provide the novel intermediate of Formula IV. This reaction is carried out in a solvent such as N,N-dimethylformamide and preferably also in the presence of a basic catalyst such as triethylamine.

In step (3), the intermediate of Formula IV is reacted with excess phosphorous oxychloride to provide the novel intermediate of Formula V.

The intermediate of Formula V is reacted in step (4) with an alkali metal alkoxide or an alkali metal alkylthiolate to provide pyrimidines of Formula VI wherein $R_5$ and/or $R_7$ is alkylthio or alkoxy.

In step (5), the compound of Formula VI is reacted with hydrazine in the presence of an inert solvent such as a lower alkanol or dioxane to provide the compound of Formula VII. The reaction is carried out be refluxing the reaction mixture.

The compound of Formula VII is acylated in step (6) using conventional methods such as reaction with an organic acid, an organic acyl halide or an organic acyl anhydride which will introduce the desired $R_3$ moiety into the molecule. The product of step (6) is the intermediate of Formula VIII.

In step (7), the intermediate of Formula VIII is cyclized to provide a compound of Formula IX. The cyclization reaction is carried out by heating the intermediate in the presence of one equivalent of phosphorous oxychloride in the presence of a solvent. Examples of suitable solvents which may be used are dioxane, 1,2-dimethoxyethane, tetrahydrofuran, benzene and the like.

In step (8) an intermediate of Formula IX wherein $R_5$ and $R_7$ are lower alkylthio may be optionally heated with an excess of a heterocyclic amine of the formula

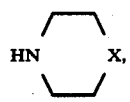

wherein X is as defined above, to provide a compound of Formula X wherein $R_7$ is alkylthio.

In step (9) a compound of Formula X wherein $R_5$ and $R_7$ are methylthio is heated with sodium methoxide in methanol to provide the compound shown.

Compounds of Formula I wherein $R_3$ is as defined above; $R_5$ is chloro, amino, lower alkylamino, di(lower alkyl)amino, lower alkylthio, lower alkoxy, mercapto, phenylthio, benzylthio or

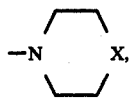

wherein X is as defined above; and $R_7$ is chloro may be prepared as follows in Reaction Scheme II:

In step (1) of Reaction Scheme II, the compound of Formula III is acylated in accordance with step (6) of Reaction Scheme I to provide the novel intermediate of Formula XI.

In step (2), the intermediate of Formula XI is cyclized by refluxing in the presence of an excess of phosphorous oxychloride. The mixture of compounds of Formula XII and XIII thereby obtained may then be separated by conventional methods such as extraction, recrystallization and chromatography to provide pure compound of Formula XII.

In step (3) the intermediate of Formula XII is reacted with a nucleophile such as an alkali metal alkoxide, an alkali metal alkylthiolate, alkali metal benzylthiolate, ammonia, a lower alkylamine, a di(lower alkyl)amine, thiourea or an amine of formula

wherein X is as defined hereinabove, to provide products of Formula XIV wherein $R_7$ is chloro.

Compounds of Formula I wherein $R_3$ is as defined above; $R_5$ is lower alkylamino, di(lower)alkylamino or

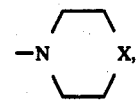

wherein X is as defined above; and $R_7$ is hydrogen or methyl, may be prepared as follows in Reaction Scheme III.

Reaction Scheme III

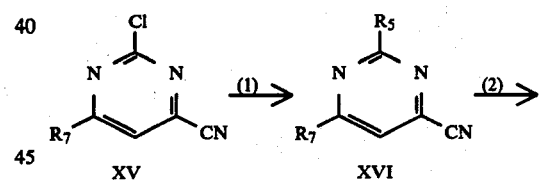

Reaction Scheme II

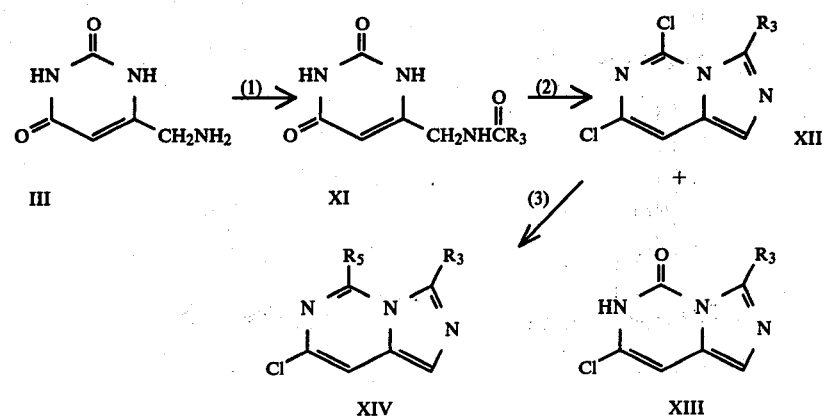

-continued
Reaction Scheme III

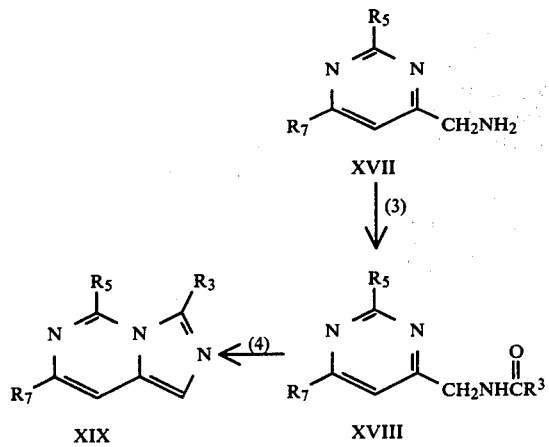

In Step (1) of Reaction Scheme III, a known 2-chloro-4-cyanopyrimidine of Formula XV is reacted with an amine which will introduce the desired $R_5$ moiety. The amine may be a lower alkylamine, di(lower)alkylamine or

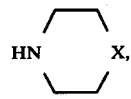

wherein X is as defined above. The product of step (1) is an intermediate of Formula XVI.

In step (2), the intermediate of Formula XVI is reacted with hydrogen gas in the presence of a suitable catalyst such as Raney nickel to provide an intermediate of Formula XVII.

In step (3), the intermediate of Formula XVII is acylated to provide an intermediate of Formula XVIII. This reaction is conducted using the method of step (6) of Reaction Scheme I.

Finally, in step (4), the intermediate of Formula XVIII is cyclized using the method of step (7) of Reaction Scheme I to provide a compound of Formula XIX.

Compounds of formula I wherein $R_3$ is as defined above; $R_5$ is methylthio and $R_7$ is lower alkoxy or lower alkylthio, may be prepared as follows in Reaction Scheme IV:

Reaction Scheme IV

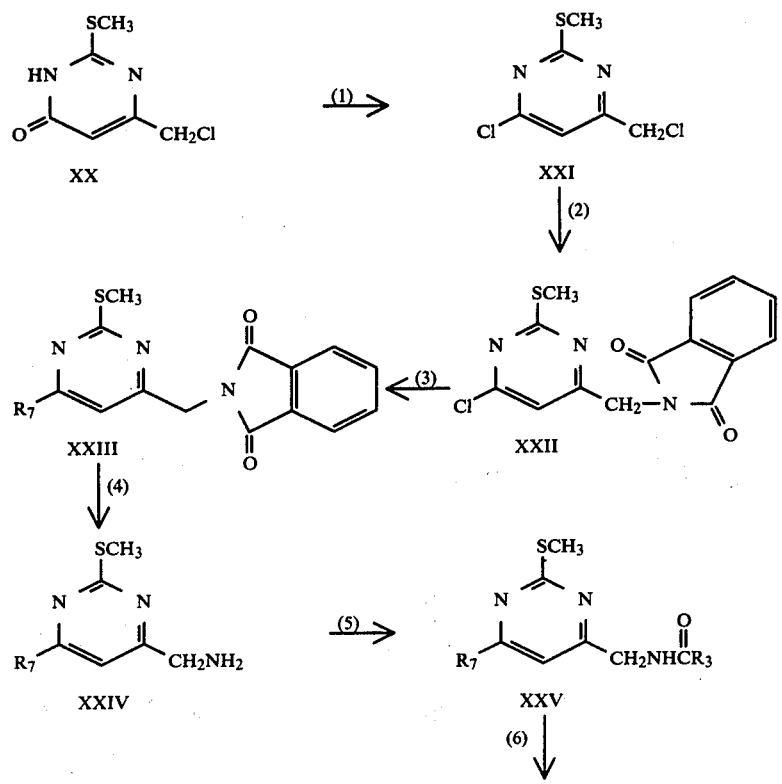

Reaction Scheme IV -continued

XXVII ← (7) ← XXVI

In step (1) of Reaction Scheme IV, a known compound of Formula XX (i.e., 6-chloromethyl-2-methylthiopyrimidine-4-one) is reacted with an excess of phosphorous oxychloride to provide a novel intermediate of Formula XXI.

The intermediate of Formula XXI is reacted in step (2) with potassium phthalimide to provide a novel intermediate of Formula XXII.

In step (3), the intermediate of Formula XXII is reacted with an alkali metal alkoxide or alkali metal alkylthiolate to provide a novel intermediate of Formula XXIII.

In step (4), the intermediate of Formula XXIII is reacted with hydrazine using the method of step (5) of Reaction Scheme I. The product is a novel intermediate of Formula XXIV.

In step (5), the intermediate of Formula XXIV is acylated to provide a novel intermediate of Formula XXV. This reaction is conducted using the method of step (6) of Reaction Scheme I.

In step (6), the intermediate of Formula XXV is cyclized using the method of step (7) of Reaction Scheme I to provide a compound of Formula XXVI.

In step (7) the novel compound of Formula XXVI is reacted with an amine of Formula

HN X, wherein X is as defined above, to provide a novel product of formula XXVII (which is a subset of Formula I).

Certain compounds of Formula I may also themselves be further reacted to provide other compounds of Formula I. The examples below contain numerous such reactions.

The following examples are provided to illustrate the synthetic methods used in the invention. They are not intended to limit the scope of the invention.

EXAMPLE 1

Part A

A mixture of 100 g (0.623 mole) of 6-chloromethylpyrimidine-2,4-dione and 200 ml of anhydrous ammonia was allowed to react overnight in a sealed bomb at about 20° C. The solid residue was slurried in ethyl acetate, and was then separated by filtration and washed sequentially with water and methanol to provide 6-aminomethylpyrimidine-2,4-dione, m.p. 295°–297° C.

Part B

To a mixture of 10.0 g (70.9 mmole) of 6-aminomethylpyrimidine-2,4-dione and 11.0 g (74.3 mmole) of phthalic anhydride in 80 ml of N,N-dimethylformamide was added 0.2 ml of triethylamine while heating at 120° C. After 2.5 hours the mixture was poured into 400 ml of an ice-water mixture. The solid was separated by filtration, washed with water and ethanol, and dried. The white solid was 6-phthalimidomethylpyrimidine-2,4-dione.

Part C

A mixture of 2.3 g (8.3 mmole) of 6-phthalimidomethylpyrimidine-2,4-dione and 50 ml of phosphorous oxychloride was heated at reflux for 4.5 hours and then cooled. The mixture was partially evaporated, then poured into 300 ml of ice-water and neutralized with solid sodium bicarbonate. The yellow solid was 2,4-dichloro-6-phthalimidomethylpyrimidine. Analysis: Calculated for $C_{13}H_7Cl_2N_3O_2$: %C, 50.67; %H, 2.29; %N, 13.64; Found: %C, 50.1; %H, 2.0; %N, 13.4. The structural assignment was confirmed by infrared and nuclear magnetic resonance spectral analyses.

Part D

To a stirred solution of sodium methoxide (prepared in 600 ml of methanol from 10.0 g (0.43 mole) of sodium metal) was added 32 ml (0.58 mole) of methanethiol and 50 g (0.162 mole) of 2,4-dichloro-6-phthalimidomethylpyrimidine. The mixture was heated at reflux for about 20 hours, then cooled. The solid was separated by filration, and washed with water and a small amount of methanol to provide a tan solid. This product was 2,4-bis(methylthio)-6-phthalimidomethylpyrimidine. The structural assignment was confirmed by infrared and nuclear magnetic resonance spectral analyses.

Part E

To a mixture of 20 g (60.4 mmole) of 2,4-bis(methylthio)-6-phthalimidomethylpyrimidine in 125 ml of ethanol and 125 ml of dioxane was added 3.5 g (70 mmole) of hydrazine hydrate, and the mixture was heated at reflux for 20 hours. The mixture was evaporated and the residue was added to 350 ml of water. To this mixture was added 10 ml of concentrated hydrochloric acid and the mixture was stirred and heated at reflux for 30 minutes. The mixture was cooled and the solid phthalhydrazide was removed by filtration. The filtrate was neutralized with ten percent aqueous sodium hydroxide solution and extracted with four 200 ml portions of chloroform. The chloroform extracts were washed with three 100 ml portions of water and 100 ml of saturated aqueous sodium chloride solution, and dried over magnesium sulfate. Evaporation provided a residue which solidified to light yellow solid 6-aminomethyl-2,4-bis(methylthio)pyrimidine.

Part F

A mixture of 11 g (16.5 mmole) of 6-aminomethyl-2,4-bis(methylthio)pyrimidine and 75 ml of acetic anhydride was stirred at room temperature for 16 hours, then evaporated. The residue was isolated by filtration and washed with a small amount of methanol to provide white solid 6-acetylaminomethyl-2,4-bis(methylthio)-pyrimidine. The structural assignment was supported by infrared spectral analysis.

Part G

To a stirred suspension of 9.00 g (37.0 mmole) of 6-acetylaminomethyl-2,4-bis(methylthio)pyrimidine in 100 ml of dioxane under nitrogen was added 7.00 g (45.7 mmole) of phosphorous oxychloride. The mixture was heated at reflux for one hour, then cooled. The solid product, 5,7-bis(methylthio)-3-methylimidazo[1,5-c]pyrimidine hydrochloride, was separated by filtration and washed with diethyl ether. This salt was mixed with 200 ml of water, and the mixture was then basified with solid sodium bicarbonate and extracted with five 50 ml portions of chloroform. The combined extracts were washed sequentially with 50 ml of water and two 50 ml portions of saturated aqueous sodium chloride solution, and were then dried over magnesium sulfate. Evaporation provided a residue which was recrystallized with treatment with decolorizing charcoal from 1:1 benzene/hexanes. The product was bright yellow solid 5,7-bis(methylthio)-3-methylimidazo[1,5-c]pyrimidine, m.p. 124°–126° C. Analysis: Calculated for $C_9H_{11}N_3S_2$: %C, 48.0; %H, 4.9; %N, 18.7; Found: %C, 48.4; %H, 4.7; %N, 19.1.

EXAMPLE 2

Part A

A mixture of 35 g (0.18 mole) of the known compound 6-chloromethyl-2-methylthiopyrimidin-4-one and 300 ml of phosphorous oxychloride was heated at reflux for 3.5 hours, cooled and evaporated. The mixture was poured into 600 ml of an ice-water mixture and the mixture was extracted with four 200 ml portions of chloroform. The combined extracts were washed sequentially with two 200 ml portions of water, 20 ml of saturated aqueous sodium bicarbonate solution and 200 ml of saturated aqueous sodium chloride solution, and were then dried over magnesium sulfate and evaporated. The residue was distilled at reduced pressure to provide 4-chloro-6-chloromethyl-2-methylthiopyrimidine as a yellow liquid, b.p. 90°–95° C./0.15 mm Hg. The structural assignment was confirmed by infrared and nuclear magnetic resonance spectral analyses.

Using the above method, 6-chloromethyl-2-methoxypyrimidin-4-one could be converted to 4-chloro-6-chloromethyl-2-methoxypyrimidine.

Part B

To a stirred solution of 32.3 g (0.155 mole) of 4-chloro-6-chloromethyl-2-methylthiopyrimidine in 100 ml of N,N-dimethylformamide was added 30.5 g (0.165 mole) of potassium phthalimide, and the mixture was stirred at 20° C. for 16 hours. The mixture was then poured into 600 ml of water, and the solid was separated by filtration and washed with water. Recrystallization from 3:2 benzene/hexane with treatment with decolorizing charcoal provided off-white 4-chloro-2-methylthio-6-phthalimidomethylpyrimidine, m.p. 174°–176° C.

Using the above method, 4-chloro-6-chloromethyl-2-methoxypyrimidine could be converted to 4chloro-2-methoxy-6-phthalimidomethylpyrimidine.

EXAMPLE 3

To 100 ml of methanol was added 1.55 g (67.4 mmole) of sodium metal to prepare 67.4 mmole of sodium methoxide. To this solution was added 20.0 g (62.6 mmole) of 4-chloro-2-methylthio-6-phthalimidomethylpyrimidine (from Example 2) and the mixture was heated at reflux for 16 hours. The mixture was cooled, and the solid was then separated by filtration. This solid was washed sequentially with methanol and water to provide 4-methoxy-2-methylthio-6-phthalimidomethylpyrimidine as a white solid. The structural assignment was confirmed by infrared and nuclear magnetic resonance spectral analyses.

Using the above method, 4-chloro-2-methoxy-6-phthalimidomethylpyrimidine could be converted to 2,4-dimethoxy-6-phthalimidomethylpyrimidine. Similarly, 4-chloro-2-methylthio-6-phthalimidomethylpyrimidine was reacted with sodium methanethiolate to provide 2,4-bis(methylthio)-6-phthalimidomethylpyrimidine, identical in all respects with the compound prepared in Example 1, part D.

EXAMPLE 4

To a mixture of 14.8 g (47.0 mmole) of 4-methoxy-2-methylthio-6-phthalimidomethylpyrimidine (from Example 3) in 100 ml of ethanol and 100 ml of dioxane was added 2.60 g (52 mmole) of hydrazine hydrate. The mixture was heated at reflux for 16 hours. The mixture was then evaporated, and the resulting residue was added to 600 ml of water. To this mixture was added 12 ml of concentrated hydrochloric acid, and the mixture was stirred and heated at reflux for 30 minutes. The mixture was cooled, and the solid phthalhydrazide obtained was removed by filtration. The filtrate was neutralized with ten percent aqueous sodium hydroxide solution and extracted with four 200 ml portions of chloroform. The chloroform extracts were washed with four 200 ml portions of saturated aqueous sodium chloride solution and were dried over magnesium sulfate. Evaporation provided a residue which was distilled under reduced pressure to provide 6-aminomethyl-4-methoxy-2-methylthiopyrimidine as a colorless liquid, b.p. 115°–117° C./0.35 mm Hg, which subsequently crystallized to a white solid, m.p. 35°–38° C. Analysis: Calculated for $C_7H_{11}N_3OS$: %C, 45.4: %H, 6.0; %N, 22.7: Found: %C, 45.4; %H, 6.0; %N, 22.8.

EXAMPLE 5

A mixture of 3.05 g (16.5 mmole) of 6-aminomethyl-4-methoxy-2-methylthiopyrimidine (from Example 4) and 50 ml of glacial acetic acid was heated at reflux for 16 hours, and was then evaporated. The residue obtained was dissolved in 20 ml of five percent aqueous sodium hydroxide solution and extracted with four 30 ml portions of chloroform. The combined extracts were washed twice with 30 ml portions of water and then with 30 ml of saturated aqueous sodium chloride solution. The combined extracts were then dried over magnesium sulfate and evaporated to provide 6-acetylaminomethyl-4-methoxy-2-methylthiopyrimidine as an off-white solid. The structural assignment was confirmed by infrared and nuclear magnetic resonance spectral analyses.

EXAMPLES 6-9

Using the method of Example 5 or a minor variation thereof where and as indicated below, the following novel intermediates of Formula XV were prepared.

TABLE I

| Example No. | Starting Material of Formula XXIV | Acyl Reactant | Intermediate of Formula XV |
|---|---|---|---|
| 6 | $SCH_3$, $N$, $N$, $CH_3O$, $CH_2NH_2$ | $HCOH$ (O) | $SCH_3$, $N$, $N$, $CH_3O$, $CH_2NHCHO$ |
| 7* | $SCH_3$, $N$, $N$, $CH_3O$, $CH_2NH_2$ | $(CH_3CH_2CH_2C)_2O$ | $SCH_3$, $N$, $N$, $CH_3O$, $CH_2NHCCH_2CH_2CH_3$ |
| 8* | $SCH_3$, $N$, $N$, $CH_3S$, $CH_2NH_2$ | $(CH_3C)_2O$ | $SCH_3$, $N$, $N$, $CH_3S$, $CH_2NHCCH_3$ |
| 9** | $SCH_3$, $N$, $N$, $CH_3S$, $CH_2NH_2$ | $C_6H_5COCl$ | $SCH_3$, $N$, $N$, $CH_3S$, $CH_2NHC(O)C_6H_5$ |

*reaction carried out at about 20° C.
**reaction carried out in chloroform and triethylamine was included as an acid acceptor.

EXAMPLE 10

To a stirred solution of sodium methoxide (prepared in 40 ml of methanol from 0.50 g (21.7 mmole) of sodium metal) was added 3.00 g (9.74 mmole) of 2,4-dichloro-6-phthalimidomethylpyrimidine (from Example 1, part C) in 10 ml of methanol. The mixture was heated at reflux for about 20 hours, and was then cooled. The solid was separated by filtration, and washed sequentially with water and a small amount of methanol to provide a white solid. This product was 2,4-dimethoxy-6-phthalimidomethylpyrimidine, m.p. 148°-149° C. Analysis: Calculated for $C_{15}H_{13}N_3O_4$: %C, 60.2; %H, 4.4; %N, 14.0; Found: %C, 59.6; %H, 4.1; %N, 13.9. The structural assignment was confirmed by infrared and nuclear magnetic resonance spectral anaylses.

EXAMPLE 11

Using the method of Example 4, 2,4-dimethoxy-6-phthalimidomethylpyrimidine (from Example 10) was converted to 6-aminomethyl-2,4-dimethoxypyrimidine.

EXAMPLE 12

A sample of 6-aminomethyl-2,4-dimethoxypyrimidine (from Example 11) was stirred at 20° C. with excess acetic anhydride and a few drops of sulfuric acid for about 20 hours. Evaporation, extraction into chloroform and reisolation provided 6-acetylaminomethyl-2,4-dimethoxypyrimidine.

Using the method of Example 1, Part G, 6-acetylaminomethyl-2,4-dimethoxypyrimidine was cyclized to provide 5,7-dimethoxy-3-methylimidazo[1,5-c]pyrimidine.

EXAMPLE 13

Using the method of Example 1, Part G, 6-(n-butanoyl)aminomethyl-4-methoxy-2-methylthiopyrimidine (from Example 7) was cyclized. The product was purified by column chromatography on silica gel and recrystallized from cyclohexane to provide yellow solid 7-methoxy-5-methylthio-3-(n-propyl)imidazo[1,5-c]pyrimidine, m.p. 98°-100° C. Analysis: Calculated for $C_{11}H_{15}N_3OS$: %C, 55.7; %H, 6.4; %N, 17.7; Found: %C, 55.5; %H, 6.4; %N, 17.4.

EXAMPLE 14

Using the method of Example 1, part G, with 1,2-dimethoxyethane as the solvent, 6-acetylaminomethyl-4-methoxy-2-methylthiopyrimidine (from Example 5) was cyclized. The yellow solid product was 7-methoxy-3-methyl-5-methylthioimidazo[1,5-c]pyrimidine, m.p. 131°-132° C. Analysis: Calculated for $C_9H_{11}N_3OS$: %C, 51.7; %H, 5.3; %N, 20.1; Found: %C, 51.9; %H, 5.1; %N, 19.9.

EXAMPLE 15

To a stirred solution of 3.0 g (21.5 mmole) of 2-chloro-4-cyanopyrimidine in 50 ml of ethanol was added 3.75 g (43 mmole) of morpholine. After stirring for 1.5 hours at about 20° C., the precipitate was separated by filtration, and washed with ethanol to provide yellow solid 4-cyano-2-(4-morpholino)pyrimidine. The structural assignment was confirmed by infrared and nuclear magnetic resonance spectral analyses.

EXAMPLES 16-18

Using the method of Example 15, the following novel intermediates, 4-cyano-6-methyl-2-(4-morpholino)pyrimidine, 4-cyano-6-methyl-2-(4-thiomorpholino)pyrimidine and 4-cyano-2-(4-thiomorpholino)pyrimidine, were prepared from the indicated starting materials and amines.

| Example | Starting Material of Formula XV | Amine | Intermediate of Formula XVI |
|---|---|---|---|
| 16 | 2-chloro-4-cyano-6-methylpyrimidine | morpholine | 4-cyano-6-methyl-2-(4-morpholino)pyrimidine |
| 17 | 2-chloro-4-cyano-6-methylpyrimidine | thiomorpholine | 4-cyano-6-methyl-2-(4-thiomorpholino)pyrimidine |
| 18 | 2-chloro-4-cyanopyrimidine | thiomorpholine | 4-cyano-2-(4-thiomorpholino)pyrimidine |

EXAMPLE 19

To a solution of 4.01 g (21.1 mmole) of 4-cyano-2-(4-morpholino)pyrimidine in 350 ml of ethanol was added about 0.5 g of Raney nickel. The mixture was hydrogenated on a Paar apparatus at 20° C. and 51 psig. After five hours, the catalyst was removed by filtration and the filtrate was evaporated to provide a residue. The product was 4-aminomethyl-2-(4-morpholino)pyrimidine.

EXAMPLES 20-22

Using the method of Example 19, the following novel intermediates were prepared from the indicated intermediates.

| Example | Intermediate of Formula XVI | Intermediate of Example XVII |
|---|---|---|
| 20 | Example 16 | 4-aminomethyl-6-methyl-2-(4-morpholino)pyrimidine |
| 21 | Example 17 | 4-aminomethyl-6-methyl-2-(4-thiomorpholino)pyrimidine |
| 22 | Example 18 | 4-aminomethyl-2-(4-thiomorpholino)pyrimidine |

EXAMPLE 23

To the crude 4-aminomethyl-2-(4-morpholino)pyrimidine was added 25 ml of 97% formic acid. The mixture was heated at reflux for three hours, and was then cooled and evaporated. The residue was taken up in a mixture of 65 ml of water and 35 ml of chloroform, and was neutralized with solid sodium bicarbonate. The organic phase was separated and the aqueous phase was extracted thrice with 35 ml portions of chloroform. The combined extracts were washed with 50 ml of water and twice with 50 ml portions of saturated aqueous sodium chloride solution and were dried over magnesium sulfate. Evaporation provided a residue which was triturated with diethyl ether. The yellow solid was separated by filtration and determined to be 4-formylaminomethyl-2-(4-morpholino)pyrimidine by infrared and nuclear magnetic resonance spectral analyses.

EXAMPLES 24-27

Using the method of Example 23, the following novel intermediates of Formula XVII were prepared from the indicated compound of Formula XVIII and the indicated acyl reactant:

| Example | Intermediate Formula XVII | Acyl Reactant | Intermediate of Formula XVIII |
|---|---|---|---|
| 24 | Example 20 | HCOH (O=) | morpholino-pyrimidine with CH3 and CH2NHCHO substituents |
| 25 | Example 20 | CH3COH (O=) | morpholino-pyrimidine with CH3 and CH2NHCOCH3 substituents |
| 26 | Example 21 | HCOH (O=) | thiomorpholino-pyrimidine with CH3 and CH2NHCHO substituents |
| 27 | Example 22 | CH3COH (O=) | thiomorpholino-pyrimidine with CH2NHCOCH3 substituent |

EXAMPLE 28

Using the method of Example 1, part G, 4-formylaminomethyl-6-methyl-2-(4-morpholino)pyrimidine was cyclized. Separation and purification by high pressure liquid chromatography provided pale yellow 7-methyl-5-(4-morpholino)imidazo[1,5-c]pyrimidine, m.p. 87°–90° C. Analysis: Calculated for $C_{11}H_{14}N_4O$: %C, 60.5; %H, 6.5; %N, 25.7; Found; %C, 60.4; %H, 6.4; %N, 26.0.

EXAMPLE 29

Using the method of Example 1, part G, with benzene as the solvent, cyclization of 4-formylaminomethyl-2-(4-morpholino)pyrimidine was carried out. Purification by column chromatography on silica gel, eluting with benzene and benzene-ethyl acetate, provided white solid 5-(4-morpholino)imidazo[1,5-c]pyrimidine, m.p. 90°–91.5° C. Analysis: Calculated for $C_{10}H_{12}N_4O$: %C, 58.8; %H, 5.9; %N, 27.4: Found: %C, 58.8; %H, 5.9; %N, 27.4.

EXAMPLE 30

Using the method of Example 1, part G, 6-benzoylaminomethyl-2,4-bis(methylthio)pyrimidine (from Example 9) was cyclized to provide yellow solid 5,7-bis(methylthio)-3-phenylimidazo[1,5-c]pyrimidine, m.p. 117°–118° C. after recrystallization from cyclohexane. Analysis: Calculated for $C_{14}H_{13}N_3S_2$: %C, 58.5; %H, 4.6; %N, 14.6; Found: %C, 58.9; %H, 4.4; %N, 14.7.

EXAMPLE 31

To a mixture 6-aminomethylpyrimidine-2,4-dione (from Example 1, Part A) in 50 ml of acetic anhydride was added two drops of concentrated sulfuric acid. The mixture was heated on a steam bath for one hour, and was then stirred overnight at about 20° C. The precipitate was separated by filtration, washed sequentially and thoroughly with water and methanol, and dried. The product was white solid 6-acetylaminomethylpyrimidine-2,4-dione. The structural assignment was confirmed by infrared and nuclear magnetic resonance analyses.

EXAMPLES 32–34

Using the method of Example 31, the following novel intermediates of Formula XI were prepared from the indicated starting materials and acyl reactants:

| Example | Starting Material of Formula III | Acyl Reactant | Intermediate of Formula XI |
|---|---|---|---|
| 32 | pyrimidinedione with CH2NH2 substituent | isobutyric anhydride | pyrimidinedione with CH2NHCOCH(CH3)2 substituent |
| 33 | pyrimidinedione with CH2NH2 substituent | n-butyric anhydride | pyrimidinedione with CH2NHCOC3H7 substituent |

| Exam- ple | Starting Material of Formula III | Acyl Reactant | Intermediate of Formula XI |
|---|---|---|---|
| 34 | HN-C(=O)-NH on pyrimidine-2,6-dione with CH$_2$NH$_2$ | 2,2-dimethylpropionic anhydride | HN-C(=O)-NH on pyrimidine-2,6-dione with CH$_2$NHC(=O)C(CH$_3$)$_3$ |

EXAMPLE 35

Part A

A suspension of 6.63 g (36.2 mmole) of 4-acetylaminomethylpyrimidine-2,6-dione in 250 ml of phosphorous oxychloride was heated at reflux for 20 hours, and was then cooled and evaporated. The residue was added to about 700 ml of cold saturated sodium bicarbonate solution. To the resulting mixture was added 200 ml of chloroform and sufficient solid sodium bicarbonate to neutralize the mixture. The solid was separated by filtration, and the filtrate was saved for Part B. The solid was washed with water and ethanol, and was then recrystallized from ethanol to provide yellow solid 7-chloro-3-methylimidazo[1,5-c]pyrimidin-5-one, m.p. 239° C. (dec.). Analysis: Calculated for $C_7H_6ClN_3O$; %C, 45.8; %H, 3.3; %N, 22.9; Found; %C, 45.8; %H, 3.1; %N, 22.8.

Part B

The filtrate from Part A was extracted with four 150 ml portions of chloroform. The combined extracts were washed twice with 150 ml of water and once with 150 ml of saturated aqueous sodium chloride solution, and were then dried over magnesium sulfate. Evaporation provided a residue which was extracted with hot benzene, which extracts were then treated with decolorizing charcoal and filtered while hot. Evaporation provided a residue which was recrystallized from cyclohexane to provide 5,7-dichloro-3-methylimidazo[1,5-c]pyrimidine, m.p. 134°–135° C. Analysis: Calculated for $C_7H_5Cl_2N_3$: %C, 41.6; %H, 2.5; %N, 20.8; Found: %C, 41.5; %H, 2.2; %N, 20.9.

EXAMPLE 36

Using the method of Example 35, Parts A and B, 4-(n-butyryl)aminomethylpyrimidine-2,6-dione was cyclized and chlorinated to provide 5,7-dichloro-3-(n-propyl)-imidazo[1,5-c]pyrimidine. Analysis: Calculated for $C_9H_9Cl_2N_3$: %C, 47.0; %H, 3.9; %N, 18.3; Found: %C, 46.4; %H, 3.7; %N, 18.4.

EXAMPLE 37

Using the method of Example 35, Parts A and B, 4-isobutyrylaminomethylpyrimidine-2,6-dione was cyclized and chlorinated to provide 5,7-dichloro-3-isopropylimidazo[1,5-c]pyrimidine, m.p. 90°–93° C. Analysis: Calculated for $C_9H_9Cl_2N_3$: %C, 47.0; %H, 3.9; %N, 18.3; Found: %C, 46.4; %H, 4.0; %H, 17.8.

EXAMPLE 38

Using the method of Example 35, Parts A and B, 4-(2,2-dimethylpropionyl)pyrimidine-2,6-dione was cyclized and chlorinated to provide 5,7-dichloro-3-(t-butyl)imidazo[1,5-c]pyrimidine, m.p. 109°–110° C. Analysis: Calculated for $C_{10}H_{11}Cl_2N_3$: %C, 49.2; %H, 4.5; %N, 17.2; Found: %C, 49.4; %H, 4.6; %N, 17.3.

EXAMPLE 39

Into a solution of 1.50 g (6.52 mmole) of 5,7-dichloro-3-isopropylimidazo[1,5-c]pyrimidine (from Example 37) in 50 ml of dioxane was bubbled ammonia gas at 20° C. for twenty minutes. The mixture was sealed and stirred for sixteen hours. Fifty ml of water and 50 ml of chloroform were added to the mixture, and the resulting organic phase was separated. The aqueous phase was extracted twice with 25 ml of chloroform. The extracts were combined and washed thrice with 50 ml portions of water, and were then dried over magnesium sulfate and evaporated. The residue of 5-amino-7-chloro-3-isopropylimidazo[1,5-c]pyrimidine was dissolved in an ethanoldiethyl ether mixture to which 0.65 g (6.6 mmole) of concentrated sulfuric acid was then added. The resulting solid was collected by filtration and dried. The product was white solid 5-amino-7-chloro-3-isopropylimidazo[1,5-c]pyrimidine dihydrogen sulfate, m.p. 164° C. (dec). Analysis: Calculated for $C_9H_{11}ClN_4.H_2SO_4$: %C, 35.0; %H, 4.2; %N, 18.2; Found; %C, 35.1; %H, 4.1; %N, 18.2.

EXAMPLE 40

Using the method of Example 39, 5,7-dichloro-3-(n-propyl)imidazo[1,5-c]pyrimidine (from Example 36) was reacted with ammonia to provide white solid 5-amino-7-chloro-3-(n-propyl)imidazo[1,5-c]pyrimidine, m.p. 160°–161° C. (dec.). Analysis: Calculated for $C_9H_{11}ClN_4$: %C, 51.3; %H, 5.3; %N, 26.6; Found %C, 51.5; %H, 5.2; %N, 26.9.

EXAMPLE 41

To a solution of 2.00 g (8.70 mmole) of 5,7-dichloro-3-isopropylimidazo[1,5-c]pyrimidine (from Example 37) in 50 ml of dioxane was added 1.15 g (19.5 mmole) of n-propylamine. The mixture was stirred for three hours. The mixture was then diluted with 75 ml of chloroform, washed with three 50 ml portions of water, dried over magnesium sulfate, and evaporated. The residue of 7-chloro-3-isopropyl-5-(n-propylamino)imidazo[1,5-c]pyrimidine was dissolved in a mixture of dioxane/diethyl ether, and hydrogen chloride gas was bubbled through. The precipitate was separated by filtration to provide white solid 7-chloro-3-isopropyl-5-(n-propylamino)imidazo[1,5-c]pyrimidine hydrochloride hydrate, m.p. 182°–184° C. Analysis: Calculated for $C_{12}H_{17}ClN_4.HCl.1/3H_2O$: %C, 48.8; %H, 6.4; %N, 19.0; Found; %C, 48.8; %H, 6.2; %N, 18.4.

EXAMPLES 42–47

Using the method of Example 39 or 41, the following compounds of Formula I were prepared from the indicated starting materials.

| Example No. | Starting Materials | Product (m.p. in °C.) |
|---|---|---|
| 42 | 5,7-dichloro-3-isopropylimidazo-[1,5-c]pyrimidine and morpholine | 7-chloro-3-isopropyl-5-(4-morpholino)imidazo[1,5-c]-pyrimidine dihydrogen sulfate (156–158) |
| 43 | 5,7-dichloro-3-isopropylimidazo-[1,5-c]pyrimidine and piperidine | 7-chloro-3-isopropyl-5-(1-piperidino)imidazo[1,5-c]-pyrimidine dihydrogen sulfate (145 dec.) |
| 44 | 5,7-dichloro-3-isopropylimidazo-[1,5-c]pyrimidine and N,N—diethylamine | 7-chloro-3-isopropyl-5-(N,N—diethylamino)imidazo-[1,5-c]pyrimidine dihydrogen sulfate (144 dec.) |
| 45 | 5,7-dichloro-3-isopropylimidazo-[1,5-c]pyrimidine and methylamine | 7-chloro-3-isopropyl-5-(N—methylamino)imidazo[1,5-c]-pyrimidine hydrochloride (207–209 dec.) |
| 46 | 5,7-dichloro-3-methylimidazo-[1,5-c]pyrimidine and morpholine | 7-chloro-3-methyl-5-(4-morpholino)imidazo-[1,5-c]pyrimidine (176–177) |
| 47 | 5,7-dichloro-3-isopropylimidazo-[1,5-c]pyrimidine and thiomorpholine | 7-chloro-3-isopropyl-5-(4-thiomorpholino)imidazo-[1,5-c]pyrimidine hydrochloride (202–203 dec.) |

EXAMPLE 48

To a stirred solution of sodium ethoxide prepared in ethanol from 0.18 g (7.8 mmole) of sodium metal under nitrogen was added 1.50 g (6.52 mmole) of 5,7-dichloro-3-isopropylimidazo[1,5-c]pyrimidine (from Example 37). After three hours at room temperature the mixture was poured into 50 ml of water and extracted thrice with 30 ml portions of chlorofrom. The combined extracts were washed thrice with 40 ml portions of water, dried over magnesium sulfate and evaporated to provide crude 7-chloro-5-ethoxy-3-isopropylimidazo[1,5-c]pyrimidine.

The free base was dissolved in a mixture of ethanol/diethyl ether and 0.40 g of concentrated sulfuric acid was added. The white solid isolated was 7-chloro-5-ethoxy-3-isopropylimidazo[1,5-c]pyrimidine dihydrogen sulfate, m.p. 144° C. (dec.). Analysis: Calculated for $C_{11}H_{14}ClN_5O \cdot H_2SO_4$: %C, 39.1; %H, 4.8; %N, 12.4; Found: %C, 38.5; %H, 4.7; %N, 12.8.

EXAMPLE 49

Using the method of Example 48, sodium methoxide was reacted with 5,7-dichloro-3-isopropylimidazo[1,5-c]pyrimidine (from Example 37) to provide 7-chloro-3-isopropyl-5-methoxyimidazo[1,5-c]pyrimidine. This free base was a white solid which was converted into its white solid dihydrogen sulfate salt, m.p. 155° C. (dec.). Analysis: Calculated for $C_{10}H_{12}ClN_3O \cdot H_2SO_4$: %C, 37.1; %H, 4.4; %N, 13.0; Found; %C, 36.7; %H, 4.2; %N, 12.9.

EXAMPLE 50

Using the method of Example 48, sodium n-propanoxide was reacted with 5,7-dichloro-3-isopropylimidazo[1,5-c]pyrimidine (from Example 37) to provide white solid 7-chloro-3-isopropyl-5-(n-propoxy)imidazo[1,5-c]-pyrimidine dihydrogen sulfate, m.p. 152° C. Analysis: Calculated for $C_{12}H_{16}ClN_3O \cdot H_2SO_4$: %C, 41.0; %H, 5.2; %N, 11.9; Found: %C, 40.9; %H, 4.9; %N, 11.9.

EXAMPLE 51

To 25 ml of methanol saturated with ammonia gas was added with stirring 1.00 g (4.35 mmole) of 5,7-dichloro-3-(n-propyl)imidazo[1,5-c]pyrimidine (from Example 36). Stirring was continued at 20° C. for 1.5 hours, at which time the mixture was poured into 50 ml of water and extracted with four 35 ml portions of chloroform. The combined extracts were washed twice with 50 ml portions of water, once with 35 ml of saturated aqueous sodium chloride solution and dried over magnesium sulfate. Concentration provided a residue which was triturated with diethyl ether to provide a yellow solid which was mostly 5-amino-7-chloro-3-(n-propyl)imidazo[1,5-c]pyrimidine. The ether solution was evaporated to provide a yellow solid. The solid was dissolved in cyclohexene, treated with decolorizing charcoal and cooled. The small amount of precipitate formed was 5-amino-7-chloro-3-(n-propyl)-imidazo[1,5-c]pyrimidine. Evaporation of the cyclohexane gave yellow solid 7-chloro-5-methoxy-3-(n-propyl)imidazo[1,5-c]pyrimidine, m.p. 76°–77° C. Analysis: Calculated for $C_{10}H_{12}ClN_3O$: %C, 53.2; %H, 5.4; %N, 18.6; Found; %C, 52.9; %H, 5.4; %N, 18.1.

EXAMPLE 52

A solution of 2.00 g (8.70 mmole) of 5,7-dichloro-3-isopropylimidazo[1,5-c]pyrimidine (from Example 37) and 0.75 g (9.9 mmole) of thiourea in 50 ml of N,N-dimethylformamide was stirred for 30 minutes, and was then poured into 150 ml of water. The mixture was basified with 10 ml of ten percent aqueous sodium hydroxide solution, stirred for ten minutes at 20° C. and filtered. The filtrate was acidified with concentrated hydrochloric acid and the resultant precipitate was collected by filtration, washed sequentially with water and ethanol and dried. The yellow solid was 7-chloro-3-isopropylimidazo[1,5-c]pyrimidine-5-thiol, m.p. 192°–193° C. Analysis: Calculated for $C_9H_{10}ClN_3S$: %C, 47.5; %H, 4.4; %N, 18.5; Found: %C, 47.3; %H, 4.5; %N, 19.0.

EXAMPLE 53

To a stirred suspension of 0.50 g (12.5 mmole) of sodium hydride in 50 ml of tetrahydrofuran at 0° C. under nitrogen was added 1.6 ml (17.7 mmole) of 2-propanethiol. After stirring for forty-five minutes at 0° C. and 15 minutes at 20° C. 1.00 g (4.35 mmole) of 5,7-dichloro-3-isopropylimidazo[1,5-c]pyrimidine (from Example 37) was added. The mixture was stirred at 20° C. under nitrogen for 2 days, and was then poured into 50 ml of an ice-water mixture. The mixture was extracted with 100 ml of chloroform and thrice with 35 ml portions of chloroform. The combined extracts were washed thrice with 75 ml portions of water and dried over magnesium sulfate. Evaporation provided a residue which was dissolved in 15 ml of ethanol. To the solution was added 0.50 g (5.1 mmole) of concentrated sulfuric acid. The resulting solution was diluted with diethyl ether. The precipitate was separated by filtration, washed with ether and dried. The white solid was 7-chloro-3-isopropyl-5-isopropylthioimidazo[1,5-c]pyrimidine dihydrogen sulfate, m.p. 172° C. (dec.). Analysis: Calculated for $C_{12}H_{16}ClN_3S \cdot H_2SO_4$: %C, 39.2; %H, 4.9; %N, 11.4; Found: %C, 39.1; %H, 5.1; %N, 11.7.

EXAMPLE 54

Using the method of Example 53, 5,7-dichloro-3-isopropylimidazo[1,5-c]pyrimidine (from Example 37) and sodium ethanethiolate were reacted to provide white solid 7-chloro-5-ethylthio-3-isopropylimidazo[1,5-c]pyrimidine dihydrogen sulfate, m.p. 162°–163° C. (dec.). Analysis: Calculated for $C_{11}H_{14}ClN_3S \cdot H_2SO_4$: %C, 37.3; %H, 4.6; %N, 11.9; Found: %C, 37.1; %H, 4.7; %N, 12.2.

EXAMPLE 55

Using the method of Example 53, 5,7-dichloro-3-isopropylimidazo[1,5-c]pyrimidine (from Example 37) and sodium benzyl mercaptide were reacted to provide white solid 5-benzylthio-7-chloro-3-isopropylimidazo[1,5-c]pyrimidine dihydrogen sulfate, m.p. 146°–148° C. (dec.). Analysis: Calculated for $C_{16}H_{16}ClN_3S \cdot H_2SO_4$: %C, 46.2; %H, 4.4; %N, 10.1; Found: %C, 46.5; %H, 4.5; %N, 10.2.

EXAMPLE 56

Using the method of Example 53, 5,7-dichloro-3-methylimidazo[1,5-c]pyrimidine (from Example 35) was reacted with sodium methanethiolate to provide yellow solid 7-chloro-3-methyl-5-methylthioimidazo[1,5-c]pyrimidine, m.p. 153°–155° C. Analysis: Calculated for $C_8H_8ClN_3S$: %C, 45.0; %H, 3.8; %N, 19.7; Found: %C, 44.8; %H, 3.5; %N, 19.7.

EXAMPLE 57

Using the method of Example 53, 5,7-dichloro-3-isopropylimidazo[1,5-c]pyrimidine (from Example 37) was reacted with sodium 1-propanethiolate to provide white solid 7-chloro-3-isopropyl-5-(1-propylthio)imidazo[1,5-c]pyrimidine dihydrogen sulfate, m.p. 160°–161° C. Analysis: Calculated for $C_{12}H_{16}ClN_3S \cdot H_2SO_4$: %C, 39.2; %H, 4.9; %N, 11.4; Found: %C, 39.1; %H, 4.9; %N, 11.9.

EXAMPLE 58

Using the method of Example 53, 5,7-dichloro-3-isopropylimidazo[1,5-c]pyrimidine (from Example 37) was reacted with sodium thiophenoxide to provide white solid 7-chloro-3-isopropyl-5-phenylthioimidazo[1,5-c]pyrimidine dihydrogen sulfate, m.p. 164°–165° C. (dec.). Analysis: Calculated for $C_{15}H_{14}ClN_3S \cdot H_2SO_4$: %C, 44.8; %H, 4.0; %N, 10.5; Found: %C, 44.7; %H, 4.3; %N, 10.2.

EXAMPLE 59

Using the method of Example 53, 5,7-dichloro-3-isopropylimidazo[1,5-c]pyrimidine (from Example 37) was reacted with sodium methanethiolate to provide white solid 7-chloro-3-isopropyl-5-methylthioimidazo[1,5-c]pyrimidine dihydrogen sulfate, m.p. 179° C. (dec.). Analysis: Calculated for $C_{10}H_{12}ClN_3S \cdot H_2SO_4$: %C, 35.3; %H, 4.2; %N, 12.4; Found; %C, 35.5; %H, 4.4; %N, 12.8.

EXAMPLE 60

To a stirred suspension of 0.10 g (2.5 mmole) of sodium hydride in 20 ml of tetrahydrofuran under nitrogen was added 0.40 g (1.8 mmole) of 7-chloro-3-isopropylimidazo[1,5-c]pyrimidine-5-thiol (from Example 52). After 20 minutes, 1.0 g (7.0 mmole) of methyl iodide was added and the mixture was stirred under nitrogen at 20° C. for 16 hours. The mixture was poured into 50 ml of water and extracted thrice with 40 ml portions of chloroform. The combined extracts were washed thrice with 50 ml of water, dried over magnesium sulfate and evaporated. Nuclear magnetic resonance spectral analysis of the crude product showed it to be 7-chloro-3-isopropyl-5-methylthioimidazo[1,5-c]pyrimidine, identical to that provided by the method of Example 59.

EXAMPLE 61

To a solution of freshly prepared sodium methoxide (0.60 g, 26.1 mmole) in 100 ml of methanol under nitrogen was added 5.0 g (22.2 mmole) of 5,7-bis(methylthio)-3-methylimidazo[1,5-c]pyrimidine (from Example 1, part G) and the mixture was heated at its reflux temperature for 1.5 hours. The mixture was poured into 300 ml of an ice-water mixture, then extracted with five 75 ml portions of chloroform. The combined extracts were dried over magnesium sulfate, then evaporated. The residue was rinsed with hexane and recrystallized from a mixture (1:2) of benzene/hexane with treatment with decolorizing charcoal. The product was pale yellow solid 5-methoxy-3-methyl-7-methylthioimidazo[1,5-c]pyrimidine, m.p. 108°–111° C. Analysis: Calculated for $C_9H_{11}N_3OS$: %C, 51.7; %H, 5.3; %N, 20.1; Found: %C, 51.7; %H, 5.1; %N, 20.4.

EXAMPLE 62

Using the method of Example 61, 5,7-bis(methylthio)-3-phenylimidazo[1,5-c]pyrimidine (from Example 30) was reacted with sodium methoxide to provide 5-methoxy-7-methylthio-3-phenylimidazo[1,5-c]pyrimidine as a pale yellow solid after recrystallization from cyclohexane, m.p. 134°–135°0 C. Analysis: Calculated for $C_{14}H_{13}N_3OS$: %C, 62.0; %H, 4.8; %N, 15.5; Found; %C, 62.0; %H, 4.7; %N, 15.7.

EXAMPLE 63

Part A

Using the method of Example 5, 6-aminomethyl-2,4-bis(methylthio)pyrimidine from Example 1, part E or Example 8 was reacted with formic acid to provide 2,4bis(methylthio)-6-formylaminomethylpyrimidine as a light yellow solid. The structural assignment was confirmed by infrared and nuclear magnetic resonance spectral analyses.

Part B

A mixture of 3.00 g (13.1 mmole) of 2,4-bis(methylthio)-6-formylaminomethylpyrimidine, 2.25 g (14.2mmole) of phosphorous oxychloride and 50 ml of dioxane was stirred at 20° C. for 20 hours, then heated at reflux for 0.5 hour. The mixture was poured into 100 ml of water, neutralized with solid sodium bicarbonate and extracted with chloroform. The chloroform extracts were combined, washed with water and dried over magnesium sulfate. Evaporation of the solvent provided a light yellow solid, 5,7-bis(methylthio)imidazo[1,5-c]pyrimidine. The structural assignment was confirmed by infrared and nuclear magnetic resonance spectral analyses.

Part C

To a solution of 0.50 g (2.37 mmole) of 5,7-bis(methylthio)imidazo[1,5-c]pyrimidine in 25 ml of ethanol was added about 0.01 g of sodium hydride and the mixture was heated at reflux for 72 hours. The mixture was partially evaporated, and was then partitioned between 30 ml of water and 30 ml of chloroform. The chloroform phase was separated and the aqueous phase was extracted with two 35 ml portions of chloroform. The combined extracts were washed thrice with 25 ml portions of water, dried over magnesium sulfate, and evaporated. The residue was an off-white solid, 5-ethoxy-7-methylthioimidazo[1,5-c]pyrimidine, m.p. 84°-88° C. The structural assignment was confirmed by comparison of the infrared spectrum and nuclear magnetic spectrum of the free base obtained in Example 48.

This is the preferred method of displacement, although Examples 61 and 62 using an equivalent of alkoxide provided some of the desired product.

EXAMPLE 64

To a cold (0° C.) mixture of 30 ml of 50% aqueous potassium hydroxide solution and 80 ml of diethyl ether was added, in small portions, 10 g (97 mmole) of 1-methyl-1-nitrosourea to generate diazomethane.

The organic layer was separated and added to a mixture of 6.00 g (32.7 mmole) of 7-chloro-3-methylimidazo[1,5-c]pyrimidin-5-one (from Example 35, part A) in 100 ml of a 1:1 mixture of ethanol/diethyl ether. Several more portions of diazomethane were obtained by adding ether to the aqueous potassium hydroxide, and separating the organic layer. These portions were added to the reaction mixture until the total volume was about 400 ml. The reaction mixture was stirred for 16 hours with the temperature initially being 0° C. and gradually being allowed to rise to about 20° C. The solid was separated by filtration. The filtrate was evaporated to provide a residue. The solids were combined and separated into fractions by high pressure liquid chromatography, eluting sequentially with dichloromethane, 5% ethyl acetate/dichloromethane and 1:1 ethyl acetate/dichloromethane. Early fractions contained small amounts of pure white solid 7-chloro-5-methoxy-3-methylimidazo[1,5-c]pyrimidine, m.p. 108°-110° C. Analysis: Calculated for $C_8H_8ClN_3O$: %C, 48.6; %H, 4.1; %N, 21.3; Found: %C, 48.3; %H, 3.9; %N, 21.1. The structural assignment was confirmed by infrared and nuclear magnetic resonance spectral analyses. Middle fractions were mixtures and later fractions contained white solid 7-chloro-3,6-dimethylimidazo[1,5-c]pyrimidin-5-one, m.p. 165°-166° C. after recrystallization from 5:3 benzene/hexane. Analysis: Calculated for $C_8H_8ClN_3O$; %C, 48.6; %H, 4.1; %N, 21.3; Found: %C, 48.7; %H, 4.0; %N, 21.4.

EXAMPLE 65

Using the method of Example 1, part G with benzene as the solvent, 4-formylaminomethyl-6-methoxy-2-methylthiopyrimidine (from Example 6) was cyclized. Purification by high pressure liquid chromatography, eluting sequentially with dichloromethane and 1:3 ethyl acetate/dichloromethane, provided a yellow solid which was recrystallized from 1:1 benzene/hexanes. The product was yellow needles of 7-methoxy-5-methylthioimidazo[1,5-c]pyrimidine, m.p. 114°-115° C. Calculated for $C_8H_9N_3OS$: %C, 49.2; %H, 4.6; %N, 21.5; Found; %C, 49.2; %H, 4.6; %N, 21.6.

EXAMPLE 66

A solution of 2.30 g (11.8 mmole) of 7-methoxy-5-methylthioimidazo[1,5-c]pyrimidine (from Example 65) in 25 ml of morpholine was heated at reflux for about 20 hours, and was then diluted with 50 ml of water and extracted four times with 35 ml portions of chloroform. The combined extracts were washed five times with 100 ml portions of water. The extracts were then dried over magnesium sulfate, treated with decolorizing charcoal, filtered and evaporated. The residue was separated by high pressure liquid chromatography, eluting with ethyl acetate. The product was recrystallized first from ethanol, then from 1:1 benzene/hexanes to provide yellow solid 5,7-bis(4-morpholino)imidazo[1,5-c]pyrimidine, m.p. 157°-159° C. Analysis: Calculated for $C_{14}H_{19}N_5O_2$: %C, 58.1; %N, 6.6; %N, 24.2; Found: %C, 58.2; %H, 6.6; %N, 23.8.

What is claimed is:

1. A compound of the formula

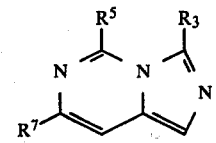

wherein $R_3$ is hydrogen, lower alkyl or phenyl; $R_5$ is chloro, amino, N-(lower)alkylamino, N,N-di(lower)alkylamino, mercapto, phenylthio, benzylthio, lower alkoxy, lower alkylthio or

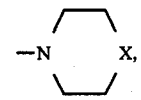

wherein X is oxygen, sulfur or methylene; and $R_7$ is hydrogen, chloro, lower alkoxy, lower alkylthio, methyl, or

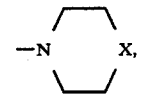

wherein X is oxygen, sulfur, or methylene; or a pharmaceutically acceptable acid addition salt thereof.

2. A compound according to claim 1, wherein $R_5$ is amino, N-(lower)alkylamino, N,N-di(lower)alkylamino, mercapto, lower alkoxy or lower alkylthio.

3. The compound 7-methoxy-5-methylthioimidazo[1,5-c]pyrimidine according to claim 1.

4. The compound 5,7-bis(methylthio)-3-methylimidazo[1,5-c]pyrimidine according to claim 1.

5. The compound 7-chloro-3-methyl-5-methylthioimidazo[1,5-c]pyrimidine according to claim 1.

6. The compound 7-chloro-3-isopropyl-5-(N-methylamino)imidazo[1,5-c]pyrimidine according to claim 1.

7. The compound 7-chloro-3-isopropylimidazo[1,5-c]pyrimidine-5-thiol according to claim 1.

8. The compound 7-chloro-3isopropyl-5-(n-propylamino)imidazo[1,5-c]pyrimidine according to claim 1.

9. The compound 5-amino-7-chloro-3-(n-propyl)imidazo[1,5-c]pyrimidine according to claim 1.

10. The compound 3-(n-propyl)-5-methylthio-7-methoxyimidazo[1,5-c]pyrimidine according to claim 1.

11. The compound 5-methoxy-7-methylthio-3-phenylimidazo[1,5c]pyrimidine according to claim 1.

12. The compound 3-methyl-7-methoxy-5-methylthioimidazo[1,5-c]pyrimidine according to claim 1.

13. The compound 7-chloro-5-methoxy-3-(n-propyl)-imidazo[1,5-c]pyrimidine according to claim 1.

14. The compound 7-chloro-5-methoxy-3-methylimidazo[1,5-c]pyrimidine.

15. A pharmaceutical composition comprising an effective amount of a compound according to claim 1 and a pharmaceutically acceptable vehicle.

16. A method for obtaining bronchodilation in a mammal wherein an effective amount of a compound according to claim 1 is administered to a mammal.

17. A method according to claim 16 wherein said compound is administered by inhalation.

* * * * *